US009861266B2

(12) United States Patent
Kinouchi

(10) Patent No.: US 9,861,266 B2
(45) Date of Patent: Jan. 9, 2018

(54) IMAGING DEVICE, ENDOSCOPE SYSTEM, AND ENDOSCOPE DEVICE

(71) Applicant: OLYMPUS CORPORATION, Tokyo (JP)

(72) Inventor: Hideaki Kinouchi, Musashino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/084,635

(22) Filed: Mar. 30, 2016

(65) Prior Publication Data

US 2016/0206185 A1      Jul. 21, 2016

Related U.S. Application Data

(63) Continuation of application No. PCT/JP2015/065947, filed on Jun. 2, 2015.

(30) Foreign Application Priority Data

Jul. 2, 2014    (JP) .................. 2014-136724

(51) Int. Cl.
*A61B 1/00*       (2006.01)
*A61B 1/04*       (2006.01)
(Continued)

(52) U.S. Cl.
CPC ............ *A61B 1/04* (2013.01); *A61B 1/00009* (2013.01); *A61B 1/00013* (2013.01);
(Continued)

(58) Field of Classification Search
CPC ... A61B 1/00013; A61B 1/00018; A61B 1/04; G02B 23/2484; H04B 10/25
See application file for complete search history.

(56) References Cited

U.S. PATENT DOCUMENTS 8,241,205 B2    8/2012  Mori et al.
2008/0039686 A1*  2/2008  Mori .................. A61B 1/00165
                                                    600/109
(Continued)

FOREIGN PATENT DOCUMENTS

JP    2002-343985 A    11/2002
JP    2002-354458 A    12/2002
(Continued)

OTHER PUBLICATIONS

International Search Report dated Aug. 18, 2015 issued in PCT/JP2015/065947.

*Primary Examiner* — Alexandra Newton
(74) *Attorney, Agent, or Firm* — Scully, Scott, Murphy & Presser, P.C.

(57) ABSTRACT

An endoscope device includes: an imaging unit for photo-electrically converting light from an object that has been irradiated with the light to generate an image signal; an optical signal converter for converting the image signal into an optical signal; a signal dividing unit for dividing the optical signal into first and second optical signals at a predetermined light quantity ratio; a first optical signal transmission line for transmitting the first optical signal; a connecting unit configured to connect the first optical signal transmission line and other optical signal transmission line and to input the first optical signal that has been transmitted through the first optical signal transmission line into the other optical signal transmission line; an electrical signal converter configured to convert the second optical signal into an electrical signal including light quantity information of the second optical signal; and an electrical signal transmission line for transmitting the electrical signal.

8 Claims, 7 Drawing Sheets

(51) Int. Cl.
*G02B 23/24* (2006.01)
*H04B 10/25* (2013.01)

(52) U.S. Cl.
CPC ...... *A61B 1/00057* (2013.01); *G02B 23/2484* (2013.01); *H04B 10/25* (2013.01)

(56) References Cited

U.S. PATENT DOCUMENTS

| | | | | |
|---|---|---|---|---|
| 2011/0292194 | A1* | 12/2011 | Kato | A61B 1/00009 348/65 |
| 2013/0012777 | A1* | 1/2013 | Baum | A61B 1/00013 600/110 |
| 2013/0096380 | A1* | 4/2013 | Matsuzawa | A61B 1/00013 600/109 |

FOREIGN PATENT DOCUMENTS

| | | |
|---|---|---|
| JP | 2003-019127 A | 1/2003 |
| JP | 2007-053675 A | 3/2007 |
| JP | 2008-036356 A | 2/2008 |
| JP | 2009-088852 A | 4/2009 |
| JP | 2009-095554 A | 5/2009 |
| JP | 2015-000173 A | 1/2015 |

* cited by examiner

IMAGING DEVICE, ENDOSCOPE SYSTEM, AND ENDOSCOPE DEVICE

CROSS REFERENCES TO RELATED APPLICATIONS

This application is a continuation of PCT international application Ser. No. PCT/JP2015/065947, filed on Jun. 2, 2015 which designates the United States, incorporated herein by reference, and which claims the benefit of priority from Japanese Patent Application No. 2014-136724, filed on Jul. 2, 2014, incorporated herein by reference.

BACKGROUND

1. Technical Field

The disclosure relates to an imaging device, an endoscope system, and an endoscope device for converting an image signal generated by an imaging unit into an optical signal and transmitting the optical signal.

2. Related Art

Conventionally, endoscope systems are used in the medical field when an organ of a subject such as a patient is observed. An endoscope system includes, for example, an endoscope including an image sensor at a distal end thereof, having a long thin shape with flexibility, and including an insertion unit to be inserted inside a body cavity of a subject and a processing device for performing image processing of an in-vivo image captured by the image sensor while connected the insertion unit via a cable and a connector and causing a display device to display the in-vivo image.

Recently, image sensors with a large number of pixels that enable clearer image observation have been developed and employing image sensors with a large number of pixels in endoscopes has been considered. Moreover, in consideration of easy introduction into a subject, it is desired to reduce a diameter of an insertion unit. Furthermore, in order to transmit signals of a large quantity at a high speed between an image sensor and a processing device with a reduced diameter of an insertion unit, employing an optical transmission system for transmitting signals using laser light has been considered also in endoscope systems (e.g. refer to JP 2008-36356 A).

SUMMARY

In some embodiments, an imaging device includes: an imaging unit having a plurality of pixels disposed in a matrix form and configured to photoelectrically convert light from an object that has been irradiated with the light to generate an image signal; an optical signal converter configured to convert the image signal into an optical signal; a signal dividing unit configured to divide the optical signal into a first optical signal and a second optical signal at a predetermined light quantity ratio; a first optical signal transmission line configured to transmit the first optical signal; a second optical signal transmission line configured to input the first optical signal that has been transmitted through the first optical signal transmission line and to transmit the first optical signal input thereto; a connecting unit configured to connect the first optical signal transmission line and the second optical signal transmission line and to input the first optical signal that has been transmitted through the first optical signal transmission line into the second optical signal transmission line; an electrical signal converter configured to convert the second optical signal into an electrical signal including light quantity information of the second optical signal; an electrical signal transmission line configured to transmit the electrical signal; and an abnormality detecting unit configured to detect whether there is an abnormality in the connecting unit based on light quantity information of the first optical signal that has been transmitted through the second optical signal transmission line and on the light quantity information of the second optical signal included in the electrical signal that has been transmitted through the electrical signal transmission line.

In some embodiments, an endoscope system is configured to be inserted into a subject to image an inside of the subject. The system includes: a light source unit configured to emit light for irradiating the inside of the subject; an imaging unit having a plurality of pixels disposed in a matrix form and configured to photoelectrically convert the light from the subject that has been irradiated with the light to generate an image signal; an optical signal converter configured to convert the image signal into an optical signal; a signal dividing unit configured to divide the optical signal into a first optical signal and a second optical signal at a predetermined light quantity ratio; a first optical signal transmission line configured to transmit the first optical signal; a second optical signal transmission line configured to input the first optical signal that has been transmitted through the first optical signal transmission line and to transmit the first optical signal input thereto; a connecting unit configured to connect the first optical signal transmission line and the second optical signal transmission line and to input the first optical signal that has been transmitted through the first optical signal transmission line into the second optical signal transmission line; an electrical signal converter configured to convert the second optical signal into an electrical signal including light quantity information of the second optical signal; an electrical signal transmission line configured to transmit the electrical signal; an abnormality detecting unit configured to detect whether there is an abnormality in the connecting unit based on light quantity information of the first optical signal that has been transmitted through the second optical signal transmission line and on the light quantity information of the second optical signal included in the electrical signal that has been transmitted through the electrical signal transmission line; and an image processing unit configured to process the image signal based on the first optical signal that has been transmitted through the second optical signal transmission line.

In some embodiments, an endoscope device includes: an imaging unit having a plurality of pixels disposed in a matrix form and configured to photoelectrically convert light from an object that has been irradiated with the light to generate an image signal; an optical signal converter configured to convert the image signal into an optical signal; a signal dividing unit configured to divide the optical signal into a first optical signal and a second optical signal at a predetermined light quantity ratio; a first optical signal transmission line configured to transmit the first optical signal; a connecting unit configured to connect the first optical signal transmission line and other optical signal transmission line and to input the first optical signal that has been transmitted through the first optical signal transmission line into the other optical signal transmission line; an electrical signal converter configured to convert the second optical signal into an electrical signal including light quantity information of the second optical signal; and an electrical signal transmission line configured to transmit the electrical signal.

The above and other features, advantages and technical and industrial significance of this invention will be better understood by reading the following detailed description of

DETAILED DESCRIPTION

Reference will be made below to an endoscope system as modes for carrying out the invention (hereinafter referred to as "embodiment(s)"). The embodiments shall not limit the invention. The same reference signs are used to designate the same elements throughout the drawings.

Embodiments

Figure 1:
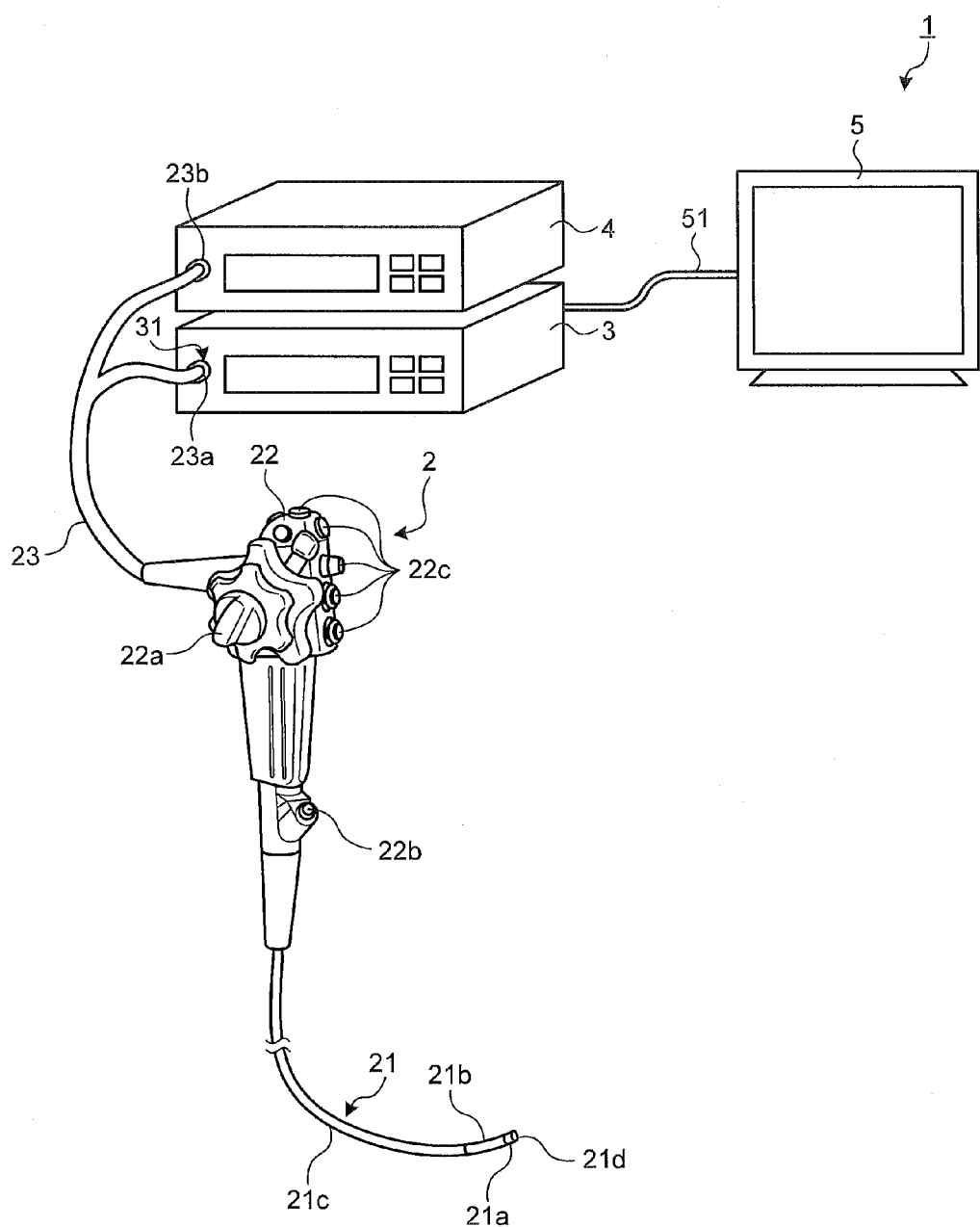
FIG. 1 is a schematic diagram illustrating an overall configuration of an endoscope system according to an embodiment of the present invention.

FIG. 1 is a schematic diagram illustrating an overall configuration of an endoscope system according to an embodiment of the present invention. As illustrated in FIG. 1, an endoscope system 1 according to the embodiments includes an endoscope 2 (scope) for capturing an inside of a body of a subject while introduced inside the subject and generating an image signal of the inside of the subject, a processing device 3 for performing predetermined image processing on the image signal captured by the endoscope 2 and controlling respective units in the endoscope system 1, a light source device 4 for generating illumination light for the endoscope 2, and a display device 5 for displaying an image from the image signal after the image processing by the processing device 3.

The endoscope 2 includes an insertion unit 21 to be inserted inside the subject, an operating unit 22 which is on a proximal end side of the insertion unit 21 and is held by an operator, and a flexible universal code 23 extending from the operating unit 22.

The insertion unit 21 is implemented by an illumination fiber (light guide cable), electrical cable, optical cable, or the like. The insertion unit 21 includes a distal end part 21a having an imaging unit incorporating an image sensor for capturing the inside of the subject, a bending part 21b freely bendable and formed of a plurality of bent pieces, and a flexible tube part 21c having flexibility and provided on a proximal end side of the bending part 21b. The distal end part 21a includes an illumination unit for illuminating the inside of the subject via an illumination lens, an observation unit for capturing the inside of the subject, an opening 21d for communicating a channel for treatment tool, and an air supply and water supply nozzle (not illustrated).

The operating unit 22 includes a bending knob 22a for causing the bending part 21b to bend in vertical and horizontal directions, a treatment tool insertion unit 22b for allowing a treatment tool such as a biopsy forceps or laser knife to be inserted in a body cavity of the subject, and a plurality of switch units 22c for performing operation of peripheral devices such as the processing device 3, light source device 4, air supply device, water supply device, and gas supply device. The treatment tool inserted from the treatment tool insertion unit 22b passes through the channel for treatment tool included in an inner part and then is exposed from the opening 21d at a distal end of the insertion unit 21.

The universal code 23 is includes an illumination fiber, electrical cable, optical cable, and the like. The universal code 23 bifurcates in a proximal end. An end part of one of the bifurcated codes forms a connector 23a while an proximal end of the other forms a connector 23b. The connector 23a is freely attachable to and detachable from a connector 31 of the processing device 3. The connector 23b is freely attachable to and detachable from the light source device 4. The universal code 23 propagates illumination light emitted from the light source device 4 to the distal end part 21a via the connector 23b, the operating unit 22, and the flexible tube part 21c. The universal code 23 transmits the image signal, captured by the imaging unit included in the distal end part 21a, the processing device 3.

The processing device 3 performs predetermined image processing on the image signal of the inside of the subject captured by the imaging unit included in the distal end part 21a in the endoscope 2. The processing device 3 controls respective units of the endoscope system 1 based on various command signals transmitted from the switch units 22c in the operating unit 22 of the endoscope 2 via the universal code 23.

The light source device 4 includes a light source for emitting light, a condenser lens, and the like. The light source device 4, under the control by the processing device 3, emits light from the light source and supplies, as illumination light to the inside of the subject as an object, to the endoscope 2 connected therewith via the connector 23b and the illumination fiber in the universal code 23.

The display device 5 includes a display or the like where liquid crystal or organic electro luminescence (EL) is used. The display device 5 displays various information including an image applied with predetermined image processing by the processing device 3 via a video cable 51. This allows the operator to operate the endoscope 2 while the operator looks at the image (in-vivo image) displayed on the display device 5, to observe a desired position inside the subject, and to judge characteristics thereof.

Figure 2:
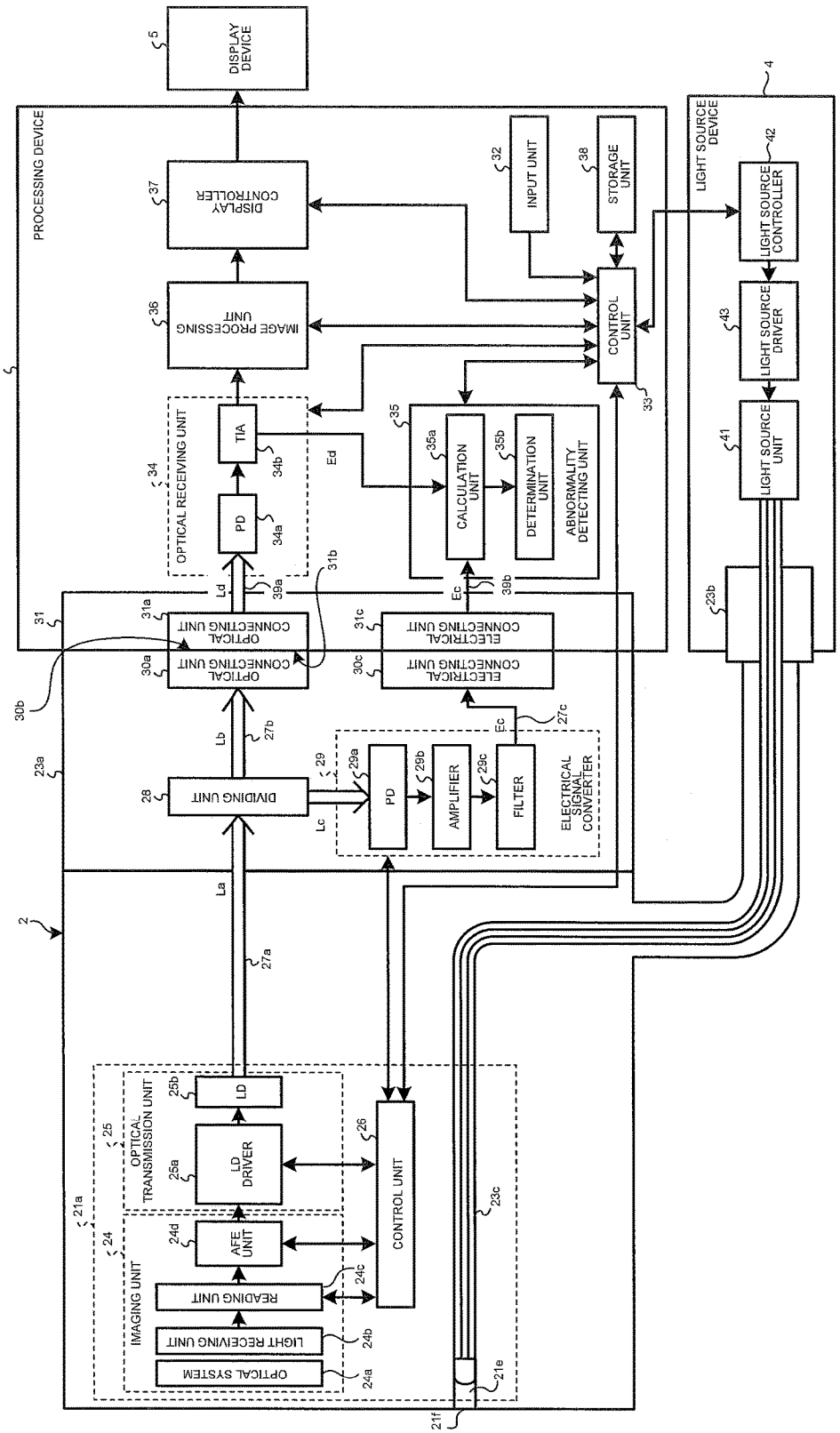
FIG. 2 is a block diagram schematically illustrating a configuration of the endoscope system illustrated in FIG. 1.

Reference will now be made to configurations of the endoscope 2, the processing device 3, and the light source device 4 having been described with reference to FIG. 1. FIG. 2 is a block diagram schematically illustrating a configuration of the endoscope system 1.

The endoscope 2 includes, in the distal end part 21a thereof, an imaging unit 24, an optical transmission unit 25 (optical signal converter), and a control unit 26. The distal end part 21a also includes a distal end of a light guide cable 23c extending from the light source device 4 via the connector 23b. The distal end of the light guide cable 23c is provided with an illumination lens 21e. Light emitted from the light source device 4 illuminates the object from an illumination window 21f in the distal end part 21a of the insertion unit 21 via the light guide cable 23c.

The imaging unit 24 includes an optical system 24a, a light receiving unit 24b, a reading unit 24c, and an analog front end (AFE) unit 24d. The imaging unit 24 includes, for example, a CCD image sensor or a CMOS image sensor.

The optical system 24a includes one or more lenses and has an optical zoom function for varying an angle of view and a focus function for varying a focus.

The light receiving unit 24b includes, on a receiving surface thereof, a plurality of pixels disposed in a matrix form for receiving light from the object irradiated with light and generating the image signal by photoelectrically converting the received light. On the receiving surface side of the light receiving unit 24b, the optical system 24a is disposed.

The reading unit 24c reads the image signal generated by the plurality of pixels in the light receiving unit 24b. The image signal read by the reading unit 24c is an electrical signal (analog).

The AFE unit 24d performs noise elimination or A/D conversion on the electrical signal of the image signal read by the reading unit 24c. The AFE unit 24d performs reduction of a noise component included in the electrical signal (analog), adjustment of amplification ratio (gain) of the electrical signal for maintaining an output level, and A/D conversion of the analog electrical signal. The image signal generated by the imaging unit 24 is output to the processing device 3 via the optical transmission unit 25, an optical cable 27a, and the connector 23a.

The optical transmission unit 25 converts the electrical signal (digital) of the image signal output from the AFE unit 24d into an optical signal and outputs the converted optical signal to the optical cable 27a. The optical transmission unit 25 includes an laser diode (LD) driver 25a for controlling driving of an LD 25b by supplying a current to the LD 25b and the LD 25b for converting the electrical signal of the image signal output from the AFE unit 24d into an optical signal (laser light).

The control unit 26 controls operations of the imaging unit 24, the optical transmission unit 25, and an electrical signal converter 29, which will be described later, according to a control signal received from the processing device 3.

The optical cable 27a transmits an optical signal La, of the image signal, obtained by the LD 25b to a dividing unit 28 in the connector 23a, which will be described later.

The endoscope 2 includes, in the connector 23a thereof, the dividing unit 28 (signal dividing unit), an optical cable 27b (first optical signal transmission line), an optical connecting unit 30a (first optical connecting unit), the electrical signal converter 29, an electrical cable 27c (electrical signal transmission line), and an electrical connecting unit 30c.

The dividing unit 28 divides the optical signal La of the image signal, obtained by the optical transmission unit 25, into an optical signal Lb (first optical signal) and an optical signal Lc (second optical signal) at a predetermined light quantity ratio. The ratio of light quantities of the optical signals obtained by the dividing unit 28 is set in a range which does not influence execution of respective image processing in the processing device 3. For example, the dividing unit 28 divides the optical signal La at a light quantity ratio of nine to one, outputs the optical signal Lb having a light quantity of 90% of the optical signal La to the optical cable 27b, and outputs the optical signal Lc having a light quantity of 10% of the optical signal La to the electrical signal converter 29.

The optical cable 27b transmits the optical signal Lb which is the first optical signal obtained by the dividing unit 28. The optical signal Lb transmitted through the optical cable 27b is output to an optical cable 39a (second optical signal transmission line) in the processing device 3, which will be described later, via the optical connecting unit 30a and an optical connecting unit 31a in the processing device 3 connected to the optical connecting unit 30a. The optical connecting unit 30a is provided on an output side of the optical cable 27b and is detachably connected to the optical connecting unit 31a which is an external member. The optical connecting unit 31a will be described later. The optical connecting unit 30a includes a GRIN lens connected to an end surface of an optical fiber in the optical cable 27b and a cover glass covering a surface of the GRIN lens.

The electrical signal converter 29 converts the optical signal Lc, which is the second optical signal obtained by the dividing unit 28, into an electrical signal Ec including the light quantity information of the optical signal Lc. The electrical signal converter 29 includes a photodiode (PD) 29a for receiving the optical signal Lc output from the dividing unit 28 and converting into an electrical signal with an intensity corresponding to a light quantity of the optical signal Lc having been received, an amplifier 29b for amplifying the electrical signal obtained by the PD 29a, and a filter 29c for removing a DC component in the electrical signal Ec. The electrical signal converter 29 may directly output the analog electrical signal or may output the electrical signal converted from analog to digital. Also, the electrical signal converter 29 may output the electrical signal with an intensity averaged for every predetermined unit time.

The electrical cable 27c transmits the electrical signal Ec obtained by the electrical signal converter 29. The electrical signal Ec transmitted through the electrical cable 27c is output to an electrical cable 39b in the processing device 3, which will be described later, via the electrical connecting unit 30c and an electrical connecting unit 31c in the processing device 3 connected to the electrical connecting unit 30c.

Next, the processing device 3 will be described. The processing device 3 includes the connector 31, an input unit 32, a control unit 33, an optical receiving unit 34 (optical signal receiving unit), an abnormality detecting unit 35, an image processing unit 36, a display controller 37, a storage unit 38, the optical cable 39a into which the first optical signal that has been transmitted through the optical cable 27b is input, and the electrical cable 39b (electrical signal transmission line).

The connector 31 includes the optical connecting unit 31a (second optical connecting unit) and the electrical connecting unit 31c. The optical connecting unit 31a is provided on an input side of the optical cable 39a and is detachably connected to the optical connecting unit 30a, which is an external member, in the connector 23a of the endoscope 2. The optical connecting unit 31a and the optical connecting unit 30a in the endoscope 2 function as a connecting unit and connect the optical cable 27b and optical cable 39a through contact between connecting surfaces 30b and 31b thereof. The optical connecting unit 31a includes a GRIN lens connected to an end surface of an optical fiber in the optical cable 39a, which will be described later, and a cover glass covering a surface of the GRIN lens. The optical connecting units 30a and 31a input the optical signal Lb transmitted through the optical cable 27b to the optical cable 39a. Hereinafter, to distinguish from the first optical signal transmitted through the optical cable 27b, the first optical signal input to the optical cable 39a via the optical connecting units 30a and 31a will be referred to as an optical signal Ld in the description below. The optical cable 39a transmits this optical signal Ld to the optical receiving unit 34.

The electrical connecting unit 31c connects the electrical cable 27c and electrical cable 39b by being connected to the electrical connecting unit 30c in the endoscope 2. The electrical signal Ec transmitted through the electrical cable 27c is input to the electrical cable 39b via the electrical connecting unit 30c and electrical connecting unit 31c in the processing device 3 connected to the electrical connecting unit 30c. The electrical cable 39b transmits this electrical signal Ec to a calculation unit 35a. Since electrical signals are not influenced by a dirt, blurring, or the like between the connecting units, it can be assumed that loss or attenuation of the electrical signal Ec between the electrical connecting units 30c and 31c hardly occurs. The electrical signal Ec transmitted to the calculation unit 35a is a second electrical signal including the light quantity information of the optical signal Lc which is the second optical signal.

The input unit 32 is implemented by an operation device such as a mouse, keyboard, touch panel, and the like and accepts input of various command information of the endoscope system 1. Specifically, the input unit 32 accepts input of subject information (e.g. ID, date of birth, and name), identification information of the endoscope 2 (e.g. ID or test items), and various command information such as a test content.

The control unit 33 is implemented by a CPU or the like. The control unit 33 controls a processing operation of respective units in the processing device 3. The control unit 33 controls operation of the processing device 3 by performing transfer or the like of data or the command information to respective configurations in the processing device 3. The control unit 33 is connected to the control unit 26 of the endoscope 2 and each element of the light source device 4 via each cable and thereby also controls operations of the imaging unit 24, the optical transmission unit 25, the electrical signal converter 29 and the light source device 4.

The optical receiving unit 34 receives the optical signal Ld transmitted through the optical cable 39a, converts the received optical signal Ld into an electrical signal Ed including light quantity information of the optical signal Ld, and outputs the electrical signal to the image processing unit 36 and the abnormality detecting unit 35. The electrical signal Ed is a first electrical signal including the light quantity information of the optical signal Ld transmitted through the optical cable 39a.

The optical receiving unit 34 includes a PD 34a for receiving and converting the optical signal Ld into an electrical signal with an intensity corresponding to the light quantity of the received optical signal Ld, and a transimpedance amplifier (TIA) 34b for performing current-to-voltage conversion on the electrical signal output from the PD 34a.

The abnormality detecting unit 35 detects whether there is an abnormality in the optical connecting units 30a and 31a which are connecting units connecting the optical cables 27b and 39a based on the light quantity information of the first optical signal Ld transmitted through the optical cable 39a and the light quantity information of the second optical signal Lc included in the electrical signal Ec transmitted through the electrical cables 27c and 39b. The abnormality detecting unit 35 includes the calculation unit 35a and a determination unit 35b.

The calculation unit 35a calculates a light quantity ratio of the optical signal Ld received by the optical receiving unit 34 and the second optical signal Lc based on the light quantity information of the first optical signal Ld transmitted through the optical cable 39a and the light quantity information of the second optical signal Lc included in the electrical signal Ec transmitted through the electrical cables 27c and 39b. The calculation unit 35a acquires the electrical signal Ed (first electrical signal) output from the optical receiving unit 34 and the electrical signal Ec (second electrical signal) transmitted through the electrical cable 39b. The electrical signal Ed includes the light quantity information of the optical signal Ld while the electrical signal Ec includes the light quantity information of the optical signal Lc. The calculation unit 35a, using an arithmetic expression reflecting respective parameters for devices along paths where the optical signals Lb, Lc, and Ld and electrical signal Ec are transmitted, performs parameter adjusting calculation processing to remove influences of the respective devices from the electrical signals Ed and Ec on at least one of the electrical signal Ed and electrical signal Ec having been acquired. Intensities of the electrical signals Ed and Ec after the parameter adjusting calculation processing directly reflect the light quantities of the optical signals Ld and Lc, respectively. Therefore, the calculation unit 35a calculates a ratio of intensities of the electrical signal Ed and electrical signal Ec as the light quantity ratio of the optical signal Lc and optical signal Ld.

Examples of parameters to be adjusted in the parameter adjusting calculation processing include a division efficiency in the dividing unit 28, an incident photon-to-current conversion efficiency in each of the PDs 29a and 34a, an amplification degree in the amplifier 29b, an efficiency of current-to-voltage conversion in the TIA 34b, attenuation ratios of optical signals in respective optical cables, etc. For example, the storage unit 38 stores the arithmetic expression used in the parameter adjusting calculation processing and a parameter table including parameters for the respective devices. The calculation unit 35a executes the parameter adjusting calculation processing using the arithmetic expression and the parameter table stored in the storage unit 38. When the electrical signal Ec has been subjected to averaging processing, the calculation unit 35a performs the same processing on the electrical signal Ed as the averaging processing performed on the electrical signal Ec and then, after averaging, calculates the ratio of intensities of the electrical signals Ed and Ec.

The determination unit 35b determines whether there is an abnormality in the optical connecting units 30a and 31a which are connecting units based on a degree of matching between the light quantity ratio of the optical signals Ld and Lc having been calculated by the calculation unit 35a and a predetermined light quantity ratio in the dividing unit 28.

The determination unit 35b determines that there is no abnormality in the optical connecting units 30a and 31a when the light quantity ratio of the optical signals Ld and Lc calculated by the calculation unit 35a substantially matches with the light quantity ratio of the optical signals obtained by the dividing unit 28. A degree of matching in the case of determining that there is no abnormality in the optical connecting units 30a and 31a is set with a predetermined range according to processing variations in the respective devices on the paths where the optical signals Lb, Lc, and Ld and electrical signal Ec are transmitted. On the other hand, the determination unit 35b determines that there is an abnormality in the optical connecting units 30a and 31a when the light quantity ratio of the optical signals Ld and Lc calculated by the calculation unit 35a does not match with the light quantity ratio of the optical signals obtained by the dividing unit 28. The display device 5 displays abnormality information indicating that there is an abnormality in the optical connecting units 30*a* and 31*a* under the control by the control unit 33 when the determination unit 35*b* determines that there is an abnormality in the optical connecting units 30*a* and 31*a*.

The image processing unit 36 performs predetermined signal processing on the image signal (electrical signal) output from the optical receiving unit 34, namely, the image signal generated by the imaging unit 24, under the control by the control unit 33. The image processing unit 36 performs, on the image signal, various image processing including optical black subtraction processing, gain adjustment processing, synchronization processing of the image signal, gamma correction processing, white balance (WB) adjustment processing, color matrix operation processing, color reproduction operation, and edge emphasis processing.

The display controller 37 generates a display image signal for display on the display device 5 from the image signal processed by the image processing unit 36. The display controller 37 converts the display image signal from a digital signal into an analog signal, changes the converted analog image signal to a format such as a high vision system, and thereby outputs to the display device 5.

The storage unit 38 is implemented by a volatile memory or a non-volatile memory and stores various programs for causing the processing device 3 and light source device 4 to operate. The storage unit 38 temporarily stores information being processed in the processing device 3. The storage unit 38 stores the image signal captured by the imaging unit 24 and the image signal subjected to the image processing by the image processing unit 36. The storage unit 38 may be configured by a memory card or the like mounted from the outside of the processing device 3.

Next, the light source device 4 will be described. The light source device 4 includes a light source unit 41, a light source controller 42, and a light source driver 43.

The light source unit 41 includes a white light source configured by a white light LED or the like and an optical system such as a condenser lens.

The light source controller 42 controls, under the control by the control unit 33 in the processing device 3, power supply by the light source driver 43 and thereby controls light emission operation of the light source unit 41.

The light source driver 43 supplies predetermined power to the light source unit 41 under the control by the light source controller 42. This allows light emitted from the light source unit 41 to illuminate the object from the illumination window 21*f* in the distal end part 21*a* of the insertion unit 21 via the connector 23*b* and the light guide cable 23*c* in the universal code 23. The imaging unit 24 is disposed near the illumination window 21*f*.

Figure 3:
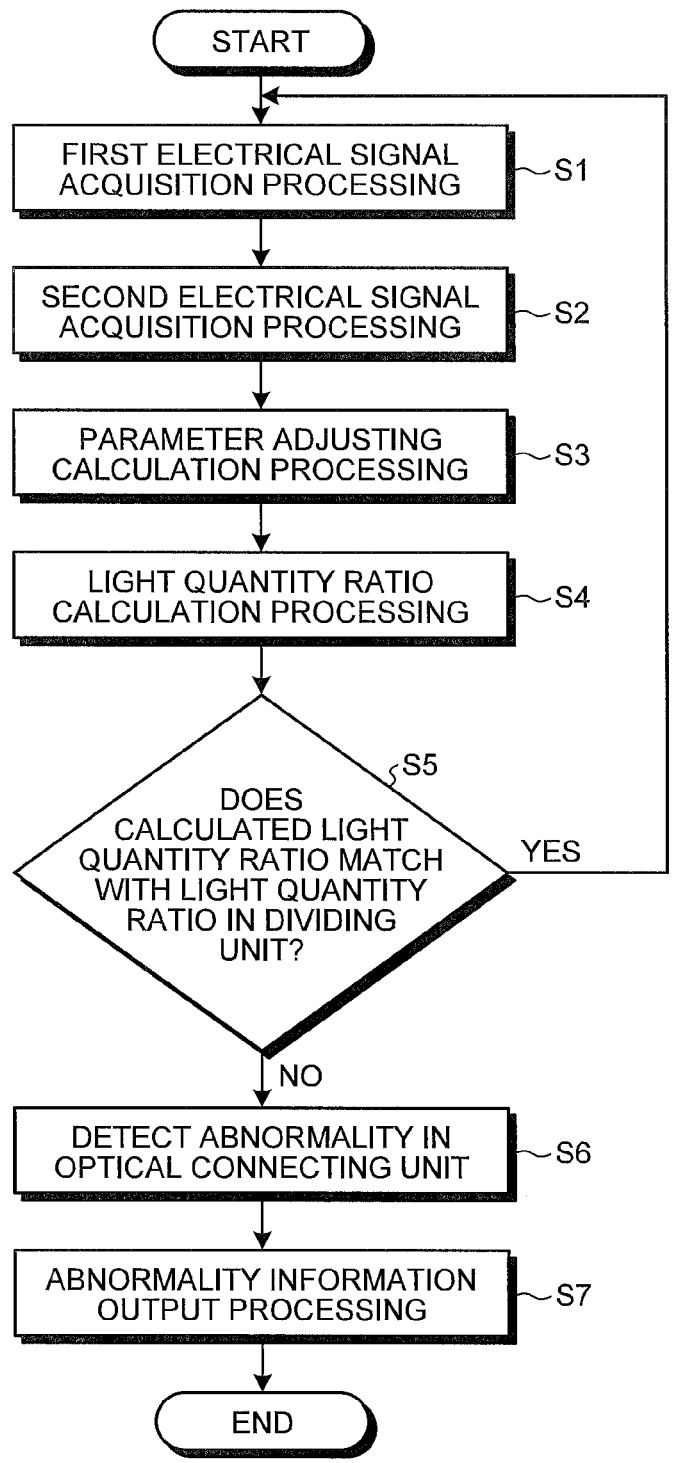
FIG. 3 is a flowchart illustrating a processing procedure of abnormality determination processing in an optical connecting unit by an abnormality detecting unit illustrated in FIG. 2.

Next, the abnormality determination processing in the optical connecting units 30*a* and 31*a* by the abnormality detecting unit 35 will be described. FIG. 3 is a flowchart illustrating a processing procedure of the abnormality determination processing in the optical connecting units 30*a* and 31*a* by the abnormality detecting unit 35.

As illustrated in FIG. 3, in the abnormality detecting unit 35, the calculation unit 35*a* performs first electrical signal acquisition processing for acquiring the first electrical signal output from the optical receiving unit 34 (step S1). In the example in FIG. 2, the calculation unit 35*a* acquires the electrical signal Ed as the first electrical signal. The calculation unit 35*a* performs second electrical signal acquisition processing for acquiring the second electrical signal transmitted through the electrical signal transmission line (step S2). In the example in FIG. 2, the electrical signal Ec transmitted through the electrical cable 39*b* is acquired as the second electrical signal. The step S1 and step S2 are in a random order and may be performed in parallel.

The calculation unit 35*a* executes the parameter adjusting calculation processing for removing influences by the respective devices within the transmission line from the electrical signals Ed and Ec using, for example, the arithmetic expression and the parameter table stored in the storage unit 38 (step S3).

The calculation unit 35*a* performs light quantity ratio calculation processing for calculating the light quantity ratio of the first optical signal received by the optical receiving unit 34 and second optical signal based on the electrical signals Ed and Ec after the parameter adjusting calculation processing (step S4). Intensities of the electrical signals Ed and Ec after the parameter adjusting calculation processing directly reflect the light quantity of the optical signal Ld which is the first optical signal received by the optical receiving unit 34 and the light quantity of the optical signal Lc which is the second optical signal, respectively. Therefore, the calculation unit 35*a* calculates a ratio of intensities of the electrical signal Ed and electrical signal Ec and outputs the calculated intensity ratio to the determination unit 35*b* as the light quantity ratio of the first optical signal and second optical signal.

The determination unit 35*b* determines whether the light quantity ratio calculated by the calculation unit 35*a* and the predetermined light quantity ratio in the dividing unit 28 substantially match with each other (step S5).

Since optical signals are easily affected by a state of an optical connecting unit connecting optical cables, when there is a dirt or blurring in one of the connecting surfaces 30*b* and 31*b* of the optical connecting units 30*a* and 31*a*, the optical signal transferred from the optical connecting unit 30*a* to the optical connecting unit 31*a* disadvantageously attenuates. As a result, the light quantity of the optical signal Ld output to the optical cable 39*a* is reduced as compared to that of the optical signal Lb immediately after division by the dividing unit 28 and the intensity of the electrical signal Ed photoelectrically converted from the optical signal Ld is also reduced as compared to that of the electrical signal photoelectrically converted directly from the optical signal Lb immediately after division by the dividing unit 28. Meanwhile, the electrical signal transmitted via the electrical connecting units 30*c* and 31*c* is not influenced by a dirt or blurring and thus an intensity of the electrical signal is not reduced. Therefore, the electrical signal Ec maintains an intensity directly reflecting the light quantity of the optical signal Lc immediately after division by the dividing unit 28. That is, the electrical signal Ec as one of operands for the ratio has a high reliability with no loss in intensity even after passing the electrical connecting units 30*c* and 31*c*.

Therefore, when the intensity ratio of the electrical signals calculated by the calculation unit 35*a*, namely the light quantity ratio, does not match with the predetermined light quantity ratio in the dividing unit 28, it can be determined that there has been attenuation in the first optical signal due to an abnormality such as a dirt or blurring in the optical connecting units 30*a* and 31*a* when the signal has passed the optical connecting units 30*a* and 31*a*.

Therefore, when the determination unit 35*b* determines that the light quantity ratio calculated by the calculation unit 35*a* and the predetermined light quantity ratio in the dividing unit 28 substantially match (step S5: Yes), the abnormality detecting unit 35 determines that there is no abnormality in the optical connecting units 30*a* and 31*a* and the flow returns to the step S1 and proceeds the abnormality detecting processing. The determination unit 35*b* determines on a degree of matching of the light quantity ratio while providing a predetermined range in consideration of variations in the respective parameters to be adjusted in the parameter adjusting calculation processing or calculation conditions.

On the other hand, when the determination unit 35b determines that the light quantity ratio calculated by the calculation unit 35a and the predetermined light quantity ratio in the dividing unit 28 do not match (step S5: No), the abnormality detecting unit 35 detects an abnormality in the optical connecting units 30a and 31a (step S6).

The abnormality detecting unit 35 outputs abnormality information indicating that there is an abnormality in the optical connecting units 30a and 31a to the control unit 33 (step S7). The control unit 33 causes the display device 5 to display an abnormality menu or the like showing that there is an abnormality such as a dirt or blurring in the optical connecting units 30a and 31a. An operator of the endoscope system 1 can promptly recognize the abnormality in the optical connecting units 30a and 31a by confirming the abnormality menu displayed on the display device 5 and can solve transmission failure of the optical signal in an early phase by cleaning the connecting surfaces 30b and 31b.

In this manner, according to the embodiment, the optical signal (image signal) is divided into the first optical signal and the second optical signal by the dividing unit 28 located at an input stage of the optical connecting units 30a and 31a and the second optical signal is then converted into an electrical signal by the electrical signal converter 29. By detecting whether there is an abnormality in the optical connecting units 30a and 31a by the abnormality detecting unit 35 based on light quantity information of the second optical signal in the converted electrical signal and light quantity information of the first optical signal transmitted via the optical cable 27b, optical connecting units 30a and 31a, and optical cable 39a, an abnormality in the optical connecting units 30a and 31a can be automatically detected, thereby allowing for solving transmission failure of the optical signal in an early phase. In the embodiments, the optical signal Ld received by the optical receiving unit 34 is directly detected and compared to the electrical signal Ec. Therefore, even when a light quantity of the laser light is extremely small or when reduction in light quantity in the optical connecting units 30a and 31a is very small, an abnormality in the optical connecting units 30a and 31a can be correctly detected.

For example, in the endoscope system 1, by executing the respective processing in FIG. 3 in a checkup before use and thereby confirming whether there is an abnormality in the optical connecting units 30a and 31a before use, the endoscope can be used after the reliability of optical transmission has been confirmed. In the endoscope system 1, of course, monitoring whether there is an abnormality in the optical connecting units 30a and 31a may also be performed by executing the respective processing in FIG. 3 during use as needed. Also, when transmission failure of the optical signal occurs during use of the endoscope system 1, executing the respective processing in FIG. 3 allows for discriminating whether the transmission failure of the optical signal is caused by a dirt or the like in the connecting surfaces of the optical connecting units 30a and 31a or caused by other configuration units.

Figure 4:
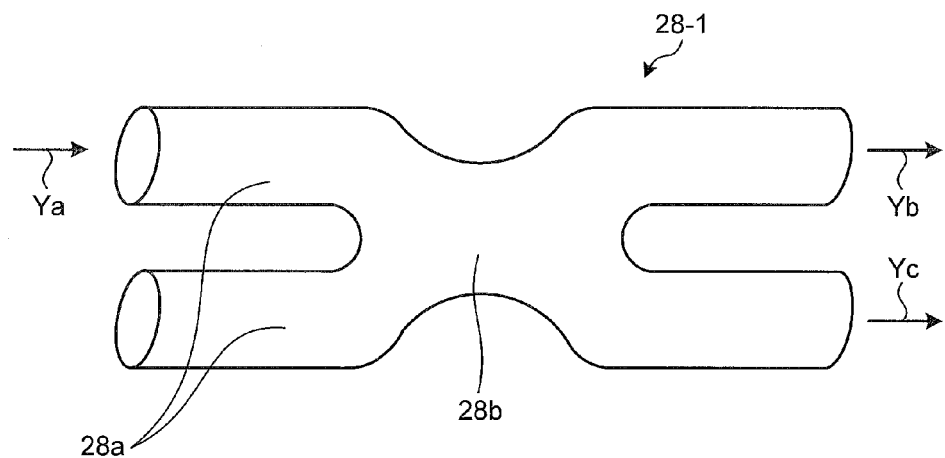
FIG. 4 is a diagram illustrating an exemplary dividing unit illustrated in FIG. 2.

The dividing unit 28 is configured by a melt drawing type splitter 28-1 (refer to FIG. 4) where two optical fibers 28a are joined by melting and drawing. An optical signal Ya input to the melt drawing type splitter 28-1 is bifurcated in a joined part 28b at a predetermined light quantity ratio. Bifurcated optical signals Yb and Yc are output from respective ports.

Figure 5:
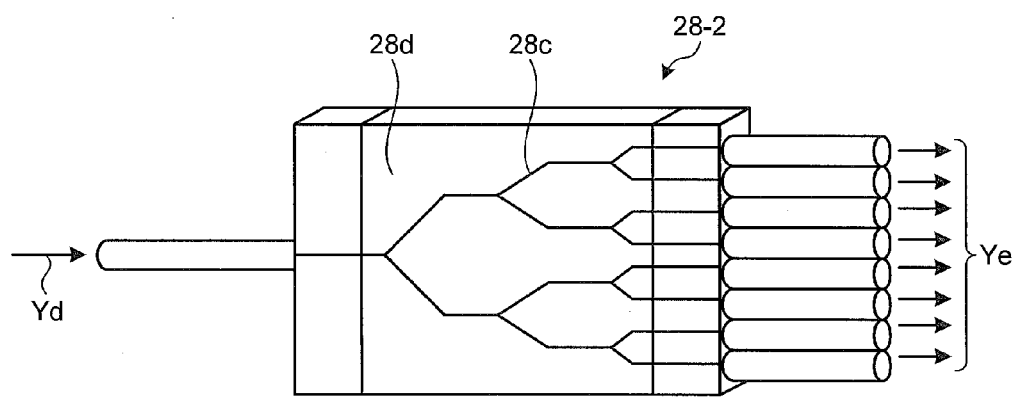
FIG. 5 is a diagram illustrating an exemplary dividing unit illustrated in FIG. 2.

Alternatively, the dividing unit 28 may be a waveguide type splitter 28-2 (refer to FIG. 5). The waveguide type splitter 28-2 includes a waveguide 28d of plate-shaped glass including an optical circuit 28c bifurcating in a Y shaped manner. An optical signal Yd input from an optical fiber connected to the waveguide 28d is bifurcated by passing a bifurcating part in the optical circuit 28c and then bifurcated respective optical signals Ye are output from respective ports.

Figure 6:
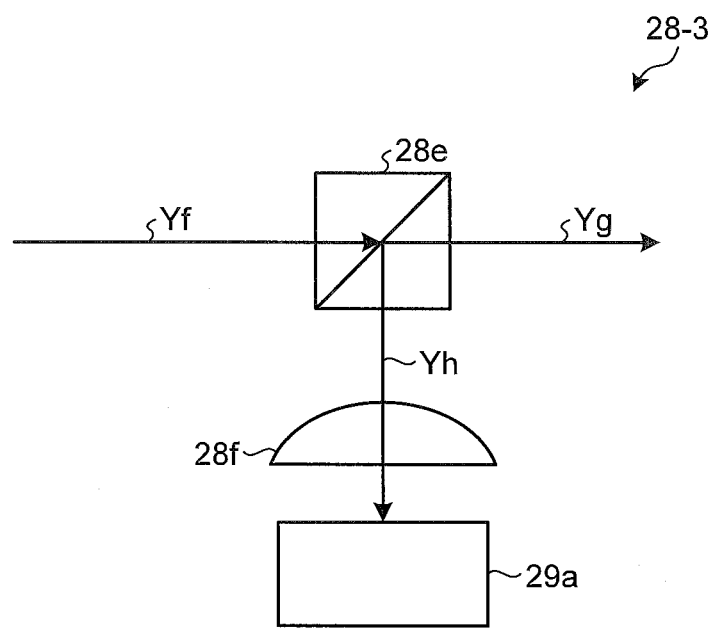
FIG. 6 is a diagram illustrating an exemplary dividing unit illustrated in FIG. 2.

Alternatively, the dividing unit 28 may be a splitter 28-3 of a beam splitter type (refer to FIG. 6). The splitter 28-3 includes a beam splitter 28e for dividing an input optical signal at a predetermined light quantity ratio. An input optical signal Yf is divided into optical signals Yg and Yh by the beam splitter 28e and thereby the signals are output. From among the output optical signals, the optical signal Yh is condensed by a cylindrical lens 28f and then input to the PD 29a. An optical system such as a collimator lens (not illustrated) is disposed at an input stage of the optical cable 27b on the output side of the optical signal Yg.

Furthermore, since it is possible for the processing device 3 to determine whether there is an abnormality in the optical connecting units 30a and 31a based on one of the divided optical signals as long as the dividing unit 28 can divide the optical signal before the optical signal passes through the optical connecting units 30a and 31a, the dividing unit 28 may be disposed at any locations at an input stage of the optical connecting units 30a and 31a as determination targets.

In the above-described embodiment, the abnormality information indicating that there is an abnormality in the optical connecting units 30a and 31a is displayed on the display device 5. Of course, the invention is not limited to the above-described embodiment. In another embodiment, an audio output device may be included in the processing device 3, thereby allowing the audio output device to output audio information indicating that there is an abnormality in the optical connecting units 30a and 31a Alternatively, an LED lump for abnormality reporting may be included and caused to be lit or to blink when there is an abnormality in the optical connecting units 30a and 31a.

Modifications of Embodiments

Figure 7:
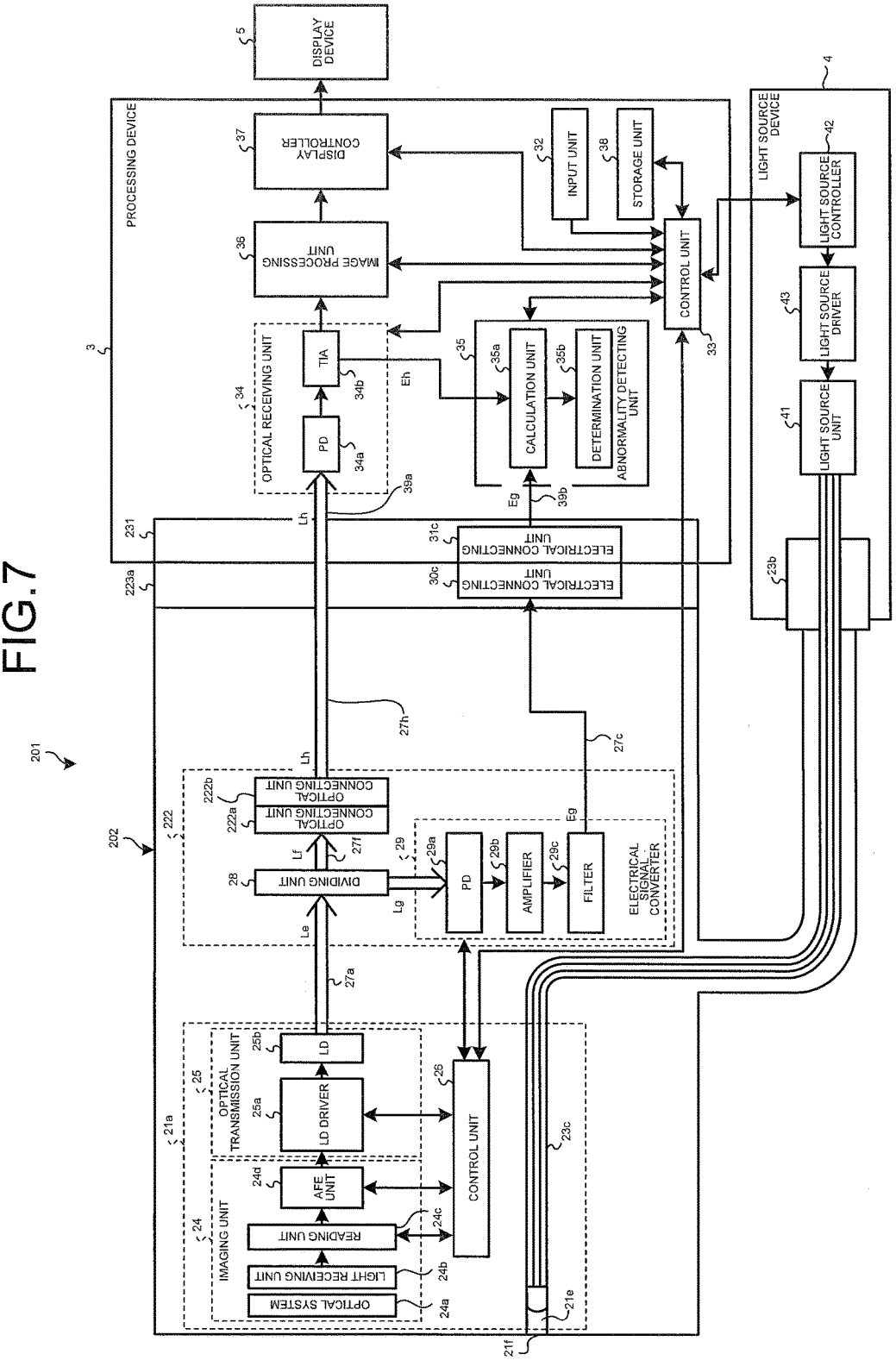
FIG. 7 is a block diagram schematically illustrating a configuration of an endoscope system according to a modification of the embodiment.

FIG. 7 is a block diagram schematically illustrating a configuration of an endoscope system according to a modification of the embodiment.

As illustrated in FIG. 7, an endoscope system 201 according to the modification of the embodiment has a configuration where optical connecting units 222a and 222b as connecting units, a dividing unit 28 and an electrical signal converter 29 are included in an operating unit 222 in an endoscope 202.

In this case, the dividing unit 28 is disposed at an input stage of the optical connecting units 222a and 222b in the operating unit 222 in order to detect whether there is an abnormality in the optical connecting units 222a and 222b. The dividing unit 28 divides an optical signal Le of an image signal obtained by an optical transmission unit 25 and transmitted through an optical cable 27a into an optical signal Lf (first optical signal) and an optical signal Lg (second optical signal) at a predetermined light quantity ratio. The dividing unit 28 outputs the optical signal Lf to an optical cable 27f (first optical signal transmission line) while outputting the optical signal Lg to the electrical signal converter 29.

The optical signal Lf transmitted through the optical cable 27f is output to an optical cable 27h (second optical signal transmission line) via the optical connecting units 222a and 222b. The optical cable 27h transmits an optical signal Lh, having passed the optical connecting units 222a and 222b, to an optical receiving unit 34. The optical receiving unit 34 converts the received optical signal Lh transmitted through an optical cable 39a into an electrical signal Eh (first electrical signal) including light quantity information of the optical signal Lh, and outputs the electrical signal to an image processing unit 36 and an abnormality detecting unit 35.

The electrical signal converter 29 converts the optical signal Lg, obtained by the dividing unit 28, into an electrical signal Eg (second electrical signal) including light quantity information of the optical signal Lg. The electrical signal Eg is input to an electrical cable 39b in a processing device 3 via an electrical cable 27c, an electrical connecting unit 30c, and electrical connecting unit 31c. The electrical cable 39b transmits the electrical signal Eg to a calculation unit 35a. Connecting a connector 223a and a connector 231 allows for connecting the endoscope 202 and processing device 3.

The abnormality detecting unit 35 performs similar processing to the processing illustrated in FIG. 3 based on the electrical signals Eh and Eg and thereby determines whether there is an abnormality in the optical connecting units 222a and 222b in the operating unit 222 for connecting the optical cables 27f and 27h.

Even with the optical connecting units 222a and 222b in the operating unit 222 in the endoscope system 201, disposing the dividing unit 28 at an input stage of the optical connecting units 222a and 222b allows the abnormality detecting unit 35 to detect an abnormality in the optical connecting units 222a and 222b based on the respective divided optical signals.

Figure 8:
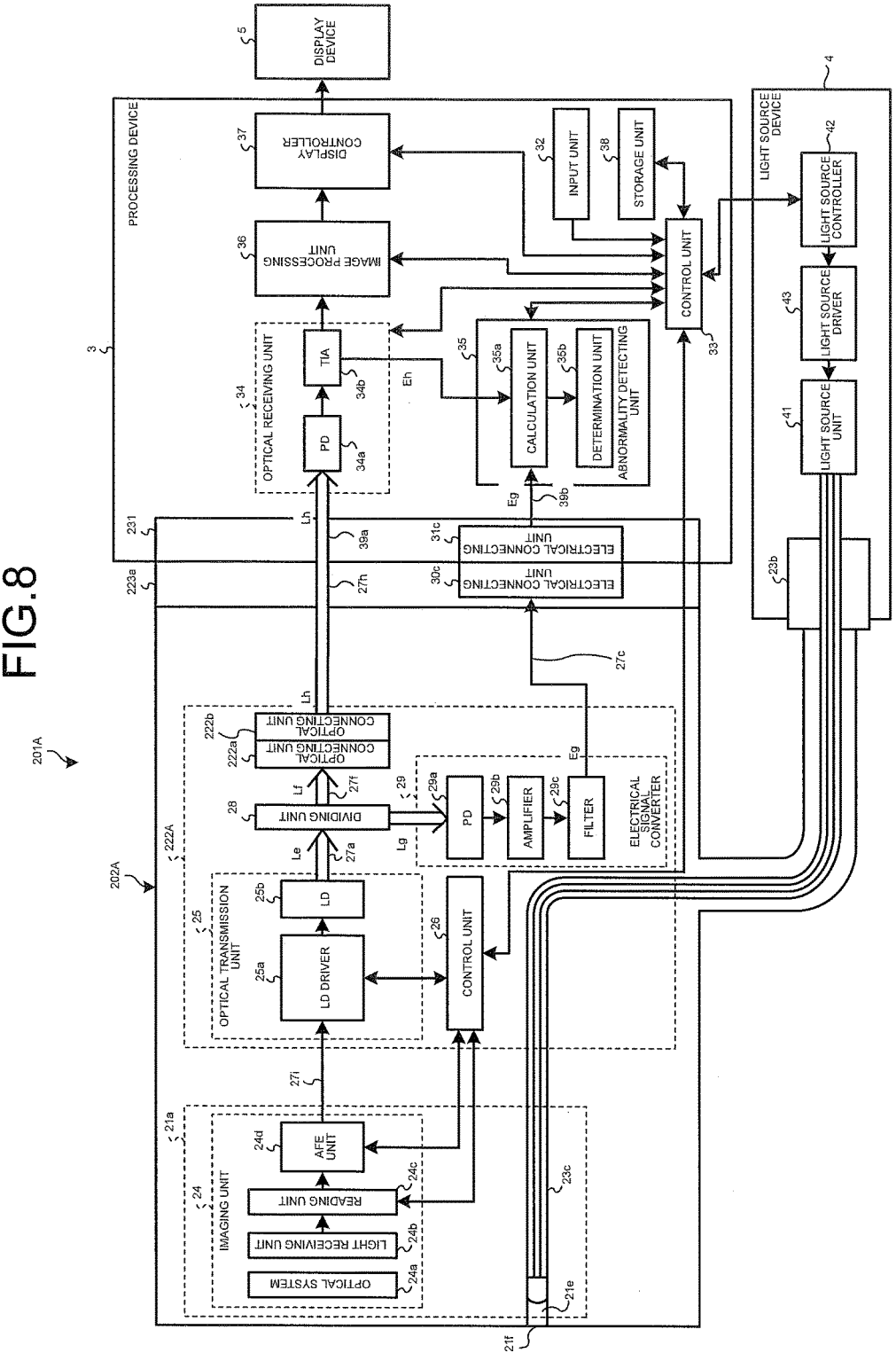
FIG. 8 is a block diagram schematically illustrating another configuration of an endoscope system according to another modification of the embodiment.

Alternatively, an endoscope system according to another modification of the embodiment may have a configuration where, as in an endoscope system 201A illustrated in FIG. 8, an optical transmission unit 25 and a control unit 26 are included in an operating unit 222A in an endoscope 202A and an image signal output from an imaging unit 24 in a distal end part 21a is transmitted to the optical transmission unit 25 via an electrical cable 27i.

Moreover, the abnormality detecting unit 35 according to the embodiments and an execution program for the respective processing executed in other configuration units of the processing device 3 may be provided by being recorded in a computer-readable storage medium such as a CD-ROM, flexible disc, CD-R, and DVD in an installable or executable file format or may be stored in a computer connected to a network such as the Internet and thereby allowing for provision by download via the network. Alternatively, provision or distribution may be carried out via a network such as the Internet.

According to some embodiments, an optical signal (image signal) is divided into a first optical signal and a second optical signal by a signal dividing unit and the second optical signal is then converted into an electrical signal by an electrical signal converter. By detecting whether there is an abnormality in a connecting unit based on light quantity information of the second optical signal in the converted electrical signal and on light quantity information of the first optical signal transmitted via a first optical signal transmission line and the connecting unit, an abnormality in the connecting unit in the optical transmission line can be detected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
an imaging unit having a plurality of pixels disposed in a matrix form and configured to photoelectrically convert light from an object that has been irradiated with the light to generate an image signal;
an optical signal converter configured to convert the image signal into an optical signal;
a signal dividing unit configured to divide the optical signal into a first optical signal and a second optical signal at a predetermined light quantity ratio;
a first optical signal transmission line configured to transmit the first optical signal;
a second optical signal transmission line configured to input the first optical signal that has been transmitted through the first optical signal transmission line and to transmit the first optical signal input thereto;
a connecting unit configured to connect the first optical signal transmission line and the second optical signal transmission line and to input the first optical signal that has been transmitted through the first optical signal transmission line into the second optical signal transmission line;
an electrical signal converter configured to convert the second optical signal into an electrical signal including light quantity information of the second optical signal;
an electrical signal transmission line configured to transmit the electrical signal; and
an abnormality detecting unit configured to detect whether there is an abnormality in the connecting unit based on light quantity information of the first optical signal that has been transmitted through the second optical signal transmission line and on the light quantity information of the second optical signal included in the electrical signal that has been transmitted through the electrical signal transmission line, wherein the abnormality detecting unit comprises a calculation unit configured to calculate a light quantity ratio between the first optical signal that has been transmitted through the second optical signal transmission line and the second optical signal, based on the light quantity information of the first optical signal that has been transmitted through the second optical signal transmission line and on the light quantity information of the second optical signal included in the electrical signal that has been transmitted through the electrical signal transmission line.

2. The imaging device according to claim 1, wherein the abnormality detecting unit comprises:
a determination unit configured to determine whether there is an abnormality in the connecting unit based on a degree of matching between the light quantity ratio calculated by the calculation unit and the predetermined light quantity ratio in the signal dividing unit.

3. The imaging device according to claim 1, wherein the connecting unit comprises:

a first optical connecting unit that is provided on an output side of the first optical signal transmission line and is configured to be detachably connected to a first external member; and a second optical connecting unit that is provided on an input side of the second optical signal transmission line and is configured to be detachably connected to a second external member, wherein the signal dividing unit, the first optical signal transmission line and the electrical signal converter are provided in the first optical connecting unit.

4. The imaging device according to claim 1, wherein the optical signal is laser light.

5. The imaging device according to claim 1, further comprising an optical signal receiving unit configured to receive the first optical signal that has been transmitted through the second optical signal transmission line and to convert the received first optical signal into an electrical signal including the light quantity information of the first optical signal to output the electrical signal, wherein the abnormality detecting unit is configured to detect whether there is an abnormality in the connecting unit based on the electrical signal output from the optical signal receiving unit and on the electrical signal that has been transmitted through the electrical signal transmission line.

6. The imaging device according to claim 1, further comprising an output unit configured to output abnormality information indicating that there is an abnormality in the connecting unit when the abnormality detecting unit detects the abnormality in the connecting unit.

7. An endoscope system configured to be inserted into a subject to image an inside of the subject, the system comprising:

a light source unit configured to emit light for irradiating the inside of the subject;

an imaging unit having a plurality of pixels disposed in a matrix form and configured to photoelectrically convert the light from the subject that has been irradiated with the light to generate an image signal;

an optical signal converter configured to convert the image signal into an optical signal;

a signal dividing unit configured to divide the optical signal into a first optical signal and a second optical signal at a predetermined light quantity ratio;

a first optical signal transmission line configured to transmit the first optical signal;

a second optical signal transmission line configured to input the first optical signal that has been transmitted through the first optical signal transmission line and to transmit the first optical signal input thereto;

a connecting unit configured to connect the first optical signal transmission line and the second optical signal transmission line and to input the first optical signal that has been transmitted through the first optical signal transmission line into the second optical signal transmission line;

an electrical signal converter configured to convert the second optical signal into an electrical signal including light quantity information of the second optical signal;

an electrical signal transmission line configured to transmit the electrical signal;

an abnormality detecting unit configured to detect whether there is an abnormality in the connecting unit based on light quantity information of the first optical signal that has been transmitted through the second optical signal transmission line and on the light quantity information of the second optical signal included in the electrical signal that has been transmitted through the electrical signal transmission line, wherein the abnormality detecting unit comprises a calculation unit configured to calculate a light quantity ratio between the first optical signal that has been transmitted through the second optical signal transmission line and the second optical signal, based on the light quantity information of the first optical signal that has been transmitted through the second optical signal transmission line and on the light quantity information of the second optical signal included in the electrical signal that has been transmitted through the electrical signal transmission line; and an image processing unit configured to process the image signal based on the first optical signal that has been transmitted through the second optical signal transmission line.

8. An endoscope device comprising:

an imaging unit having a plurality of pixels disposed in a matrix form and configured to photoelectrically convert light from an object that has been irradiated with the light to generate an image signal;

an optical signal converter configured to convert the image signal into an optical signal;

a signal dividing unit configured to divide the optical signal into a first optical signal and a second optical signal at a predetermined light quantity ratio;

a first optical signal transmission line configured to transmit the first optical signal;

a connecting unit configured to connect the first optical signal transmission line and other optical signal transmission line and to input the first optical signal that has been transmitted through the first optical signal transmission line into the other optical signal transmission line;

an electrical signal converter configured to convert the second optical signal into an electrical signal including light quantity information of the second optical signal;

an electrical signal transmission line configured to transmit the electrical signal; and an abnormality detecting unit configured to detect whether there is an abnormality in the connecting unit based on light quantity information of the first optical signal that has been transmitted through the second optical signal transmission line and on the light quantity information of the second optical signal included in the electrical signal that has been transmitted through the electrical signal transmission line, wherein the abnormality detecting unit comprises a calculation unit configured to calculate a light quantity ratio between the first optical signal that has been transmitted through the second optical signal transmission line and the second optical signal, based on the light quantity information of the first optical signal that has been transmitted through the second optical signal transmission line and on the light quantity information of the second optical signal included in the electrical signal that has been transmitted through the electrical signal transmission line.

* * * * *